United States Patent [19]

Mixan

[11] Patent Number: 4,487,933

[45] Date of Patent: Dec. 11, 1984

[54] TITANIUM CATALYZED TRANSESTERIFICATION

[75] Inventor: Craig E. Mixan, Midland, Mich.

[73] Assignee: The Dow Chemical Company, Midland, Mich.

[21] Appl. No.: 491,680

[22] Filed: May 5, 1983

Related U.S. Application Data

[63] Continuation of Ser. No. 330,366, Dec. 14, 1981, abandoned.

[51] Int. Cl.³ .............................................. C07D 213/64
[52] U.S. Cl. .................................... 546/302; 546/301
[58] Field of Search ................................ 546/302, 301

[56] References Cited

FOREIGN PATENT DOCUMENTS 2117760A 10/1983 United Kingdom ................ 546/302

OTHER PUBLICATIONS

Kato et al., Chem. Abstracts, vol. 79, (17), Abst. 104,959s, Oct. 29, 1973.

*Primary Examiner*—Alan L. Rotman

[57] ABSTRACT

Ether cleavage in transesterifications of pyridyloxyphenoxy alkanoic acid compounds is reduced by employing titanium compounds as catalysts.

11 Claims, No Drawings

TITANIUM CATALYZED TRANSESTERIFICATION

This is a continuation of application Ser. No. 330,366, filed Dec. 14, 1981, now abandoned.

BACKGROUND OF THE INVENTION

1. Field of the Invention

Transesterifications are equilibrium reactions and are subject to acid or base catalysis. Ether linkages can also be susceptible to both acid and base cleavage and, in such cases, for each ether linkage cleaved, two new impurities can be formed when attempting transesterifications of ether containing substrates.

2. Description of Prior Art

Substituted-2-pyridyloxyphenoxy alkane carboxylic acids and their derivatives are known compounds having utility as herbicides. Such products are described in, for example, European Pat. No. 483 and British Pat. No. 1,599,121.

The various derivatives of such acids do not necessarily have the same efficacy or effectiveness against different plant species and, accordingly, it is sometimes desirable to modify the molecule to obtain the desired results. However, when transesterifications of, for example, 2-(4-((3-chloro-5-(trifluoromethyl)-2-pyridyl)oxy)phenoxy)propanoic acid esters, such as transesterifying the methyl ester to the butyl ester, are carried out to high conversions with conventional acid and base transesterification catalysts, e.g., toluene sulfonic acid, ion exchange resins, sodium methoxide, sodium carbonate and potassium carbonate, from 0.5 to 2.2 percent or more pyridyl ether cleavage is obtained. With higher boiling alcohols, the ether cleavage becomes a more severe problem, with the combined impurities produced by ether cleavage approaching 10 percent.

SUMMARY OF THE INVENTION

It has now been found that in the transesterification reaction

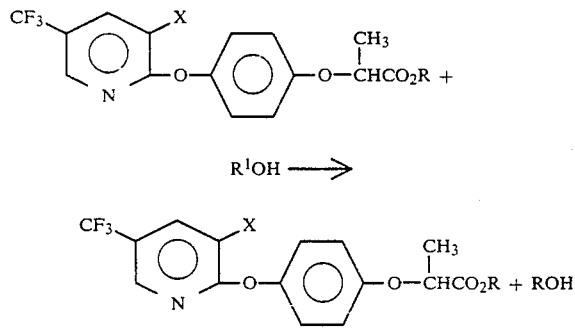

wherein x is hydrogen or chlorine, R is a $C_1$–$C_8$ straight or branched chain alkyl group or a group $C_2H_4(OC_2H_4)_xOR^2$, $CH(CH_3)CH_2[OCH(CH_3)CH_2]_x$-$OR^2$ or $CH_2CH(CH_3)[OCH(CH_3)CH_2]_xOR^2$ where x is 0–1 and $R^2$ is a $C_1$–$C_4$ straight or branched chain alkyl group and $R^1$ is a $C_2$–$C_8$ straight or branched chain alkyl group or a group $C_2H_4(OC_2H_4)_nOR^3$, $CH(CH_3)CH_2[OCH(CH_3)CH_2]_nOR^3$ or $CH_2CH(CH_3)[OCH(CH_3)CH_2]_nOR^3$ where n is 0–2 and $R^3$ is a straight or branched chain alkyl group having 1 to 4 carbon atoms, the cleavage of the ether linkages is reduced to the yields of the desired transesterified product are improved when one employs a titanium catalyst from the group $TiO_2$, $TiCl_4$ or $Ti(OR^4)_4$ where $R^4$ is alkyl and where ROH and $R^4OH$ are lower boiling than $R^1OH$ or where $R^4$ is $R^1$.

The reaction is advantageously carried out in a reactor equipped with an efficient stirrer, a distillation column and a reflux splitter-condenser assembly. The reactor is charged with the starting ester to be transesterified and the appropriate higher-boiling alcohol to form the desired ester product. The mixture is dried by distillation of the reactant alcohol and the catalyst is then introduced into the reaction mixture, which is heated to the boiling point of the reactant alcohol. The by-product alcohol is continuously removed by distillation with an appropriate reflux ratio to prevent undue loss of the higher boiling reactant alcohol. After completion of the ester interchange, the catalyst can be hydrolyzed by the addition of small amounts of water or by the addition of charcoal and water. The neutralized catalyst is then removed by filtration. Evaporation and recovery of excess alcohol gives the desired ester of high purity in virtually quantitative yield.

The catalysts are advantageously employed in an amount of from about 0.01 to about 3.0 weight percent, preferably 0.05 to 0.3 weight percent, based on the weight of the starting ester. The reactant alcohol is advantageously employed in an amount of from about 2 to about 20 equivalents, preferably 3 to 10 equivalents, of alcohol based on moles of starting ester.

Although the specific temperature employed is dependent on the boiling point of the reactant alcohol, the reaction is advantageously carried out at 80° to 200° C., preferably 100° to 150° C.

The pressure is preferably atmospheric pressure, although higher or lower pressures may be employed to adjust the boiling point into the preferred temperature range. The reaction time may be from less than one hour to 50 hours, depending on catalyst level, reaction temperature, alcohol concentration and type of alcohol.

The invention is further illustrated by the following examples.

EXAMPLE 1

In a 250 ml three-necked flask equipped with a magnetic stirrer, distillation column and reflux head was charged 100 g (1.35 moles) of BuOH. The solvent was dried by distilling BuOH until the overhead temperature reached 116° C. 2-(4-((3-Chloro-5(trifluoromethyl)-2-pyridyl)oxy)phenoxy)propanoic acid, methyl ester (38 g, 0.1 mole) and titanium tetrabutoxide (0.04 g, 0.11 weight percent) were then introduced and the mixture was heated to 118° C. while MeOH was stripped overhead. After 1½ hours, the reaction mixture was stripped of excess butanol under reduced pressure to give 42.1 g butyl ester of 99 percent purity.

EXAMPLE 2

In a 250 ml flask equipped with a magnetic stirrer, distillation column and reflux head was charged 100 g of 2-butoxyethanol. The solvent was dried by distilling the alcohol under reduced pressure until the overhead temperature reached 119° C. at 150 mm Hg. The vacuum was released with dry $N_2$ and 38.0 g (0.1 mole) of the methyl ester employed in Example 1 and 0.04 g (0.11 weight percent) of titanium tetrabutoxide were introduced. The mixture was heated at 125° C. at 150 mm Hg while MeOH was stripped overhead. After three hours, the mixture was stripped of excess alcohol at reduced pressure to give 46.6 g of product that contained 96.6 percent 2-butoxyethyl ester, 0.4 percent methyl ester and 0.9 percent acid.

EXAMPLE 3

In a 125 ml flask equipped with a magnetic stirrer, distillation column and reflux splitter was charged 15 g (0.0398 mole) of the methyl ester employed in Example 1 and 40 g (0.44 mole) of 1-methyl-2-methoxyethanol. The mixture was dried by distilling alcohol until the overhead temperature reached 119° C. Titanium tetrabutoxide (0.02 g, 0.13 weight percent) was introduced and the mixture was heated while MeOH was stripped overhead. After 16 hours at 124° C., the mixture was cooled to 90° C. and a small amount of charcoal and a few drops of water were added to hydrolyze the catalyst. The mixture was filtered to remove catalyst and the solvent was evaporated under reduced pressure to give 15.8 g of 1-methyl-2-methoxyethyl ester of 99 percent purity.

EXAMPLE 4

In a 3 liter, three-necked flask equipped with a mechanical stirrer, 10-plate Oldershaw column and reflux splitter was charged 685 g (1.82 moles) of the methyl ester employed in Example 1 and 1100 g of 2-ethoxy ethanol. The mixture was dried by distilling alcohol with a 5:1 reflux ratio until the overhead temperature reached 130° C. After drying, 0.4 g (0.06 weight percent) of titanium tetrabutoxide was added. The mixture was heated to 140° C. and methanol was removed overhead, at first a 2:1 and then a 5:1 reflux ratio. After 2½ hours, the excess alcohol was stripped under reduced pressure to give 792.6 g of 2-ethoxyethyl ester of 99.2 percent purity. The ester has a melting point of 59° to 60.5° C.

EXAMPLE 5

In a 500 ml flask equipped with a magnetic stirrer, 10-plate Oldershaw column and reflux splitter was charged 200 g (0.48 mole) of the butyl ester of the propanoic acid compound of Example 1 and 133 g (1.48 moles) of 2-ethoxyethanol. The mixture was dried by distilling the alcohol until the overhead temperature reached 130° C. After drying, 0.1 g (0.05 weight percent) of titanium tetrabutoxide was added and the mixture was heated to 145° to 150° C. while BuOH was stripped overhead at a reflux ratio of 5:1. After 14 hours, the excess alcohol was stripped under reduced pressure to give 205 g of product which contained 94.4 percent 2-ethoxyethyl ester and 4.8 percent butyl ester.

EXAMPLE 6

In a 125 ml flask equipped with a magnetic stirrer, distillation column and reflux splitter was charged 40 g (0.54 mole) of BuOH. The solvent was dried by distilling alcohol until the overhead temperature reached 115° C. The methyl ester employed in Example 1 (10 g, 0.0265 mole) and titanium tetrabutoxide (0.3 g, 3 weight percent) were added and the mixture was heated to 117° C. while MeOH was stripped overhead. After one hour, the excess alcohol was stripped under reduced pressure to give 10.9 g of butyl ester of 97 percent purity.

EXAMPLE 7

In a 125 ml flask equipped with a magnetic stirrer, distillation column and reflux splitter was charged 40 g (0.54 mole) of BuOH and 0.25 g (2.5 weight percent) titanium dioxide. The mixture was dried by distilling alcohol until the overhead temperature reached 115° C. The methyl ester employed in Example 1 (10 g, 0.0265 mole) was added and the mixture was refluxed. After 31 hours, the reaction mixture was cooled and TiO₂ was removed by filtration. Evaporation of excess alcohol under reduced pressure gave 9.6 g of butyl ester of 98.4 percent purity.

EXAMPLE 8

In a 125 ml flask equipped with a magnetic stirrer, distillation column and reflux splitter was charged 10 g (0.0265 mole) of the methyl ester employed in Example 1 and 40 g (0.54 mole) of BuOH. The mixture was dried by distilling alcohol until the overhead temperature reached 115° C. Titanium tetrachloride (0.1 g, 1 weight percent) was added and the reaction mixture was heated at 118° C. while MeOH was stripped overhead. After three hours, the reaction mixture was cooled to 80° C. and several drops of water were added to neutralize the catalyst. After cooling to ambient temperature, the catalyst was removed by filtration through Celite. Evaporation of excess alcohol under reduced pressure gave 10.6 g of butyl ester of 99 percent purity.

EXAMPLE 9

In a 125 ml flask equipped with a magnetic stirrer, distillation column and reflux splitter was charged 10 g (0.0265 mole) of the methyl ester employed in Example 1 and 25 g (0.28 mole) of 2-methoxy-1-propanol. The mixture was dried by distilling alcohol until the overhead temperature reached 130° C. After drying, 0.01 g (0.1 weight percent) of titanium tetrabutoxide was introduced and the mixture was heated to 136° C. while MeOH was stripped overhead. After three hours, the reaction mixture is cooled to 90° C. and a small amount of charcoal and several drops of water were added to hydrolyze the catalyst. After cooling to room temperature, the catalyst is removed by filtration. Evaporation of excess alcohol under reduced pressure gave 10.3 g of 2-methoxy-1-propyl ester of 99.4 percent purity.

EXAMPLE 10

In a 500 ml three-necked flask equipped with a magnetic stirrer, distillation column and reflux splitter was charged 187 g (0.45 mole) of the butyl ester of the propanoic acid compound of Example 1 and 190 g (2.11 mole) of 2-ethoxyethanol. The mixture was dried by distilling alcohol until the overhead temperature reached 130° C. After drying, 0.1 g (0.05 weight percent) of titanium tetra-iso-propoxide was added and the mixture was heated at 140° to 146° C. while methanol was stripped overhead. After three hours, the mixture contained 94.6 percent 2-ethoxyethyl ester and 4.6 percent butyl ester.

Various modifications may be made in the present invention without departing from the spirit or scope thereof and it is understood that I limit myself only as defined in the appended claims.

I claim:

1. A process for transesterifying compounds having the formula

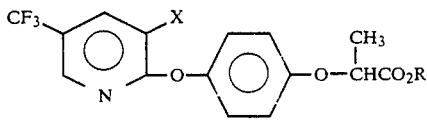

wherein X is hydrogen or chlorine, R is a $C_1$–$C_8$ straight or branched chain alkyl group or a group $C_2H_4(OC_2H_4)_xOR^2$, $CH(CH_3)CH_2[OCH(CH_3)CH_2]_xOR^2$ or $CH_2CH(CH_3)[OCH(CH_3)CH_2]_xOR^2$ where x is 0–1 and $R^2$ is a $C_1$–$C_4$ straight or branched chain alkyl group which consists essentially of reacting said compounds under substantially anhydrous conditions and at a temperature of from 80° to 150° C. with an alcohol having the formula $R^1OH$ wherein $R^1$ is a $C_2$–$C_8$ straight or branched chain alkyl group or a group $C_2H_4(OC_2H_4)_nOR^3$, $CH(CH_3)CH_2[OCH(CH_3)CH_2]_nOR^3$ or $CH_2CH(CH_3)[OCH(CH_3)CH_2]_nOR^3$ where n is 0–2 and $R^3$ is a straight or branched chain alkyl group having 1 to 4 carbon atoms in the presence of a catalyst selected from $TiO_2$, $TiCl_4$ or $Ti(OR^4)_4$ where $R^4$ is alkyl and where ROH and $R^4OH$ are lower boiling than $R^1OH$ or where $R^4$ is $R^1$.

2. Process of claim 1 where x is chlorine.
3. Process of claim 2 where R is methyl.
4. Process of claim 3 where $R^1$ is —$C_2H_4OC_2H_5$.
5. Process of claim 3 where $R^1$ is butyl.
6. Process of claim 3 where $R^1$ is —$C_2H_4OC_4H_9$.
7. Process of claim 3 where $R^1$ is —$CH(CH_3)CH_2OCH_3$.
8. Process of claim 3 where $R^1$ is —$CH_2CH(OCH_3)CH_3$.
9. Process of claim 4 where the catalyst is $TiCl_4$.
10. Process of claim 4 where the catalyst is $Ti(O\text{-iso-propyl})_4$.
11. Process of claim 4 where the catalyst is $Ti(O\text{-butyl})_4$.

* * * * *